(12) United States Patent
Sakai et al.

(10) Patent No.: US 8,939,018 B2
(45) Date of Patent: Jan. 27, 2015

(54) ANALYZING DEVICE AND METHOD FOR CONTROLLING SAME

(75) Inventors: Toshikatsu Sakai, Kyoto (JP); Akira Sezaki, Kyoto (JP); Takeshi Takagi, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 524 days.

(21) Appl. No.: 13/122,059

(22) PCT Filed: Oct. 2, 2009

(86) PCT No.: PCT/JP2009/067217
§ 371 (c)(1),
(2), (4) Date: Mar. 31, 2011

(87) PCT Pub. No.: WO2010/038853
PCT Pub. Date: Apr. 8, 2010

(65) Prior Publication Data
US 2011/0185797 A1 Aug. 4, 2011

(30) Foreign Application Priority Data
Oct. 3, 2008 (JP) .................. 2008-258703

(51) Int. Cl.
*G01N 30/16* (2006.01)
*G01N 30/20* (2006.01)
*G01N 30/18* (2006.01)
*G01N 30/86* (2006.01)
*G01N 30/04* (2006.01)

(52) U.S. Cl.
CPC ............ *G01N 30/20* (2013.01); *G01N 30/18* (2013.01); *G01N 30/8665* (2013.01); *G01N 30/8658* (2013.01); *G01N 2030/042* (2013.01); *G01N 2030/201* (2013.01); *G01N 2030/202* (2013.01); *G01N 2030/207* (2013.01)
USPC ......................................................... 73/61.58

(58) Field of Classification Search
CPC ................................. G01N 30/16; G01N 30/20
USPC ......................................................... 73/61.56
See application file for complete search history.

(56) References Cited

U.S. PATENT DOCUMENTS

| 5,417,853 | A | * | 5/1995 | Mizuno et al. | 210/198.2 |
| 5,920,006 | A | * | 7/1999 | Zelechonok | 73/61.56 |
| 5,922,106 | A | * | 7/1999 | Mowry et al. | 95/87 |
| 6,402,946 | B1 | * | 6/2002 | Spraul et al. | 210/198.2 |
| 2002/0174713 | A1 | * | 11/2002 | Petro et al. | 73/61.52 |
| 2007/0277596 | A1 | * | 12/2007 | Kim et al. | 73/61.48 |

FOREIGN PATENT DOCUMENTS

| DE | 4139683 A1 | 6/1992 |
| EP | 0892267 A1 | 1/1999 |
| JP | 58-30870 U | 2/1983 |

(Continued)

*Primary Examiner* — Hezron E Williams
*Assistant Examiner* — Mark A Shabman
(74) *Attorney, Agent, or Firm* — Fox Rothschild LLP

(57) ABSTRACT

An analyzing device includes a feeder connected to a container in which a sample is contained for sucking the sample from the container and feeding the sample, and a controller for performing control for feeding from the feeder to a measurer. In measuring the sample, the controller performs control so that results of a plurality of times of measurement are obtained with respect to the single container in which the sample is contained, without changing the container. This arrangement allows quick accuracy check.

4 Claims, 5 Drawing Sheets

(56) References Cited

FOREIGN PATENT DOCUMENTS

| | | |
|---|---|---|
| JP | 63-307356 A | 12/1988 |
| JP | 05-034328 A | 2/1993 |
| JP | 10-096715 A | 4/1998 |
| JP | 10096715 A * | 4/1998 ............ G01N 30/16 |
| WO | 2004/113873 A2 | 12/2004 |
| WO | 2005/048126 A2 | 5/2005 |
| WO | 2009/111228 A2 | 9/2009 |

* cited by examiner

ANALYZING DEVICE AND METHOD FOR CONTROLLING SAME

INCORPORATION BY REFERENCE

This application is a 371 of International Application No. PCT/JP2009/067217 filed Oct. 2, 2009, which claims priority to Japanese Patent Application No. 2008-258703 filed Oct. 3, 2008, the entire contents of which being hereby incorporated herein by reference.

TECHNICAL FIELD

The present invention relates to an analyzing device used as an analysis means in the field of biochemistry, medicine and the like. The invention also relates to a control method for checking the accuracy of such a device. The invention is particularly related to liquid chromatography.

BACKGROUND ART

In recent years, liquid chromatography devices are often used for sample analysis in the field of organic chemistry, biochemistry, medicine or the like. An example of a liquid chromatography device is disclosed in e.g. Patent Document 1. FIG. 5 shows the structure of a typical liquid chromatography device. The illustrated liquid chromatography device X includes a column 91, a detector 92, a liquid feed pump 93, an injection valve 94, a sample suction nozzle 95 and a suction unit 96. The liquid feed pump 93 is attached to a mobile phase container B containing a mobile phase such as an eluant and can feed the eluant to the column 91 via the injection valve 94. The sample suction nozzle 95 is attached to a sample container C containing a sample. The suction unit 96 is used to draw the sample into the injection valve 94.

The liquid chromatography device X is controlled by a controller, not shown. The controller controls the device so that the eluant is fed by the liquid feed pump 93 into the column 91 after the sample drawn into the injection valve 94 is adsorbed to the filler in the column 91 and then measurement is performed by the detector 92. The sample adsorbed to the filler is desorbed by the eluant and separated into components within the column 91. The detector 92 detects each separated component by e.g. measuring the absorbance.

With respect to such a liquid chromatography device X, the measurement accuracy of the device needs to be regularly checked for stable working of the device. For instance, to check the accuracy, two sample containers C one of which contains a sample of a known higher concentration and the other one of which contains a sample of a known lower concentration are prepared, and concentration measurement is performed with respect to each sample container under the above-described control by the controller, to check if correct measurement result corresponding with the known concentration is obtained with respect to each container. In a clinical site, for example, such accuracy check needs to be performed in the morning, during which a lot of other works need to be done. Thus, it is desirable that the accuracy check can be completed quickly. However, with the conventional liquid chromatography device X, the measurement for accuracy check takes much time, because the nozzle or the like needs to be cleaned every time the sample is changed.

Moreover, to check the accuracy of the device more precisely, the measurement of a sample of a known concentration for such accuracy check is usually performed a plurality of times, e.g. three times, with respect to each concentration. To perform measurement a plurality of times with the liquid chromatography device X, a large number of sample containers need to be prepared, which requires much time for sample preparation and much cost.

Patent Document 1: JP-A-H10-96715

DISCLOSURE OF THE INVENTION

Problems to be Solved by the Invention

The present invention has been proposed under the circumstances described above. It is therefore an object of the present invention to provide an analyzing device which allows quick accuracy check and reduction in cost for accuracy check, and to provide a controlling method for the device. The invention particularly relates to a problem with a liquid chromatography device, among various analyzing devices.

Means for Solving the Problem

According to a first aspect of the present invention, there is provided an analyzing device comprising: a feeder connected to a container in which a sample is contained, where the feeder is configured to suck the sample from the container and feeding the sample; and a controller for performing control for feeding the sample from the feeder to a measurer. In measuring the sample, the controller performs control so that results of a plurality of times of measurement are obtained with respect to the single container in which the sample is contained, without changing the container.

In a preferred embodiment of the present invention, the feeder includes a tubular portion capable of retaining in it the sample of an amount necessary for two or more times of measurement. The controller first performs control so that part of the sample retained by the feeder is fed to the measurer, and then, after a single time of measurement, the controller performs control so that at least part of the remaining sample retained by the feeder is fed to the measurer.

In a preferred embodiment of the present invention, the analyzing device comprises a liquid chromatography device in which: the measurer includes a column containing a filler, and an injection valve capable of introducing a predetermined amount of sample into the column and also capable of feeding a mobile phase into the column, the measurer being configured so that the sample adsorbed to the filler is desorbed by the mobile phase and an effluent thereby produced is subjected to measurement for obtaining measurement results; the feeder is configured to feed the sample to the injection valve; and in checking accuracy by using a sample of a known concentration as the sample, the controller performs control so that results of a plurality of times of measurement are obtained with respect to the single container in which the sample of the known concentration is contained, without changing the container.

In a preferred embodiment of the present invention, the feeder includes a tubular portion capable of retaining in it the sample of an amount necessary for two or more times of measurement as a result of a single time of suction of the sample from the container. The controller first performs control so that part of the sample retained by the feeder is fed to the column via the injection valve, and then, after a single time of measurement, the controller performs control so that at least part of the remaining sample retained by the feeder is fed to the column via the injection valve.

According to a second aspect of the present invention, there is provided a method of controlling an analyzing device comprising a feeder connected to a container in which a sample is contained for sucking the sample from the container and feeding the sample, and a measurer to which the sample is fed from the feeder. The method comprises performing control, in measuring the sample, so that results of a plurality of times of measurement are obtained with respect to the single container in which the sample is contained, without changing the container.

In a preferred embodiment of the present invention, the feeder includes a tubular portion capable of retaining in it the sample of an amount necessary for two or more times of measurement. The method comprises first performing control so that part of the sample retained by the feeder is fed to the measurer, and then, after a single time of measurement, performing control so that at least part of the remaining sample retained by the feeder is fed to the measurer.

In a preferred embodiment of the present invention, the analyzing device comprises a liquid chromatography device in which: the measurer includes a column containing a filler, and an injection valve capable of introducing a predetermined amount of sample into the column and also capable of feeding a mobile phase into the column, the measurer being configured so that the sample adsorbed to the filler is desorbed by the mobile phase and an effluent thereby produced is subjected to measurement for obtaining measurement results; and the feeder is configured to feed the sample to the injection valve. The method comprises performing control, in checking accuracy by using a sample of a known concentration as the sample, so that results of a plurality of times of measurement are obtained with respect to the single container in which the sample of the known concentration is contained, without changing the container.

In a preferred embodiment of the present invention, the feeder includes a tubular portion capable of retaining in it the sample of an amount necessary for two or more times of measurement. The method comprises first performing control so that part of the sample retained by the feeder is fed to the column via the injection valve, and then, after a single time of measurement, performing control so that at least part of the remaining sample retained by the feeder is fed to the column via the injection valve.

Other features and advantages of the present invention will become more apparent from the detailed description given below with reference to the accompanying drawings.

BEST MODE FOR CARRYING OUT THE INVENTION

Preferred embodiments of the present invention are described below with reference to the accompanying drawings.

Figure 1:
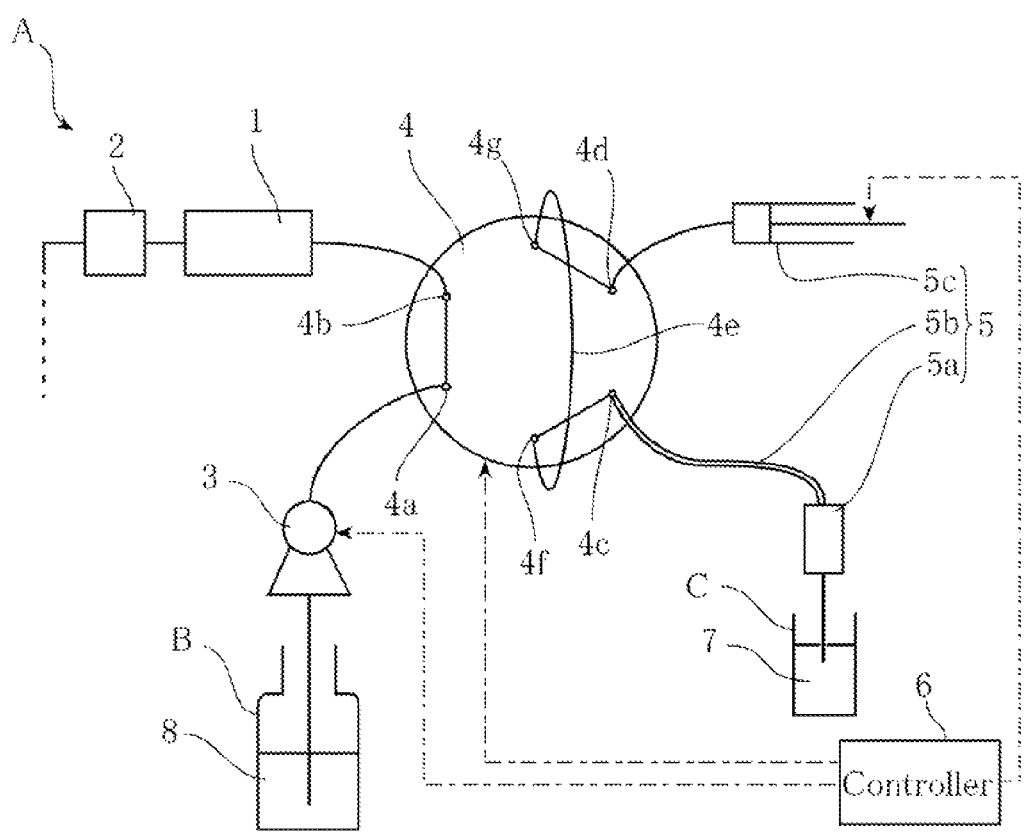
FIG. 1 is a structural view showing an example of liquid chromatography device according to the present invention.

FIG. 1 is a structural view showing an example of liquid chromatography device according to the present invention. The liquid chromatography device A shown in FIG. 1 includes a column 1, a detector 2, a liquid feed pump 3, an injection valve 4, a feeder 5 and a controller 6. The liquid chromatography device A separates a sample into components for analysis by using an eluant 8, which is a mobile phase.

The column 1 contains filler for adsorbing a sample 7 introduced into the column. After the sample 7 is adsorbed to the filler, the eluant 8 is introduced into the column 1, whereby the adsorbed sample 7 is desorbed by the eluant 8. The desorbed sample 7 and the eluant 8 flow through the column 1 as an effluent and are then discharged.

The detector 2 performs e.g. measurement of absorbance with respect to the effluent flowing in the column 1 to analyze the components of the sample 7.

The liquid feed pump 3 is attachable to a mobile phase container B and feeds the eluant 8 from the mobile phase container B to the column 1 under control by the controller 6. The liquid feed pump 3 is also used to feed the sample 7 within the injection valve 4 to the column 1.

The injection valve 74 comprises e.g. a six-way valve and includes ports 4a, 4b, 4c, 4d, 4f, 4g and an injection loop 4e. The valve further includes individual fluid paths between the ports 4a and 4b, between the ports 4c and 4f, and between the ports 4d and 4g. Portions of the injection valve 4 except the injection loop 4e are rotatable under control by the controller 6 so that connection target of the ports 4a, 4b, 4c, 4d, 4f, 4g can be changed. In order for the liquid feed pump 3 to feed the eluant 8 to the column 1, the port 4a is connected to the liquid feed pump 3, whereas the port 4b is connected to the column 1. In this state, the eluant 8 flows into the column 1 through the fluid path between the ports 4a and 4b. The injection loop 4e is configured to connect the ports 4f and 4d or the ports 4a and 4d. The injection loop 4e is capable of storing a sample 7 of a predetermined amount necessary for a single time of measurement. For instance, the amount of the sample 7 necessary for a single time of measurement is 5 μm.

The feeder 5 is provided to feed the sample 7 from the sample container C to the injection valve 4 under control by the controller 6 and includes a sample suction nozzle Sa, a tubular portion 5b and a suction unit Sc. For instance, 400 μL of sample 7 is stored in the sample container C. The sample suction nozzle 5a is attached to the sample container C to draw the sample 7 into the tubular portion 5b. In the state shown in FIG. 1, the port 4c is connected to the tubular portion 5b, whereas the port 4d is connected to the suction unit 5c. The tubular portion 5b is capable of storing the sample 7 of an amount necessary for at least three times of measurement, and has a volume of e.g. about 400 μL. The suction unit 5c draws the sample 7 through the sample suction nozzle 5a into the tubular portion 5b under control by the controller 6. The suction unit 5c further draws the sample 7 stored in the tubular portion 5b into the injection loop 4e connected to the ports 4f and 4g of the injection valve 4.

Apart from the control during normal measurement, the controller 6 is capable of performing special control for checking the accuracy of the liquid chromatography device A. The accuracy check is performed by measuring the concentration of a sample 7 of a known concentration three times and checking whether the measurement results correspond with the known concentration. The control method for this accuracy check is described below with reference to FIGS. 2-4.

Figure 2:
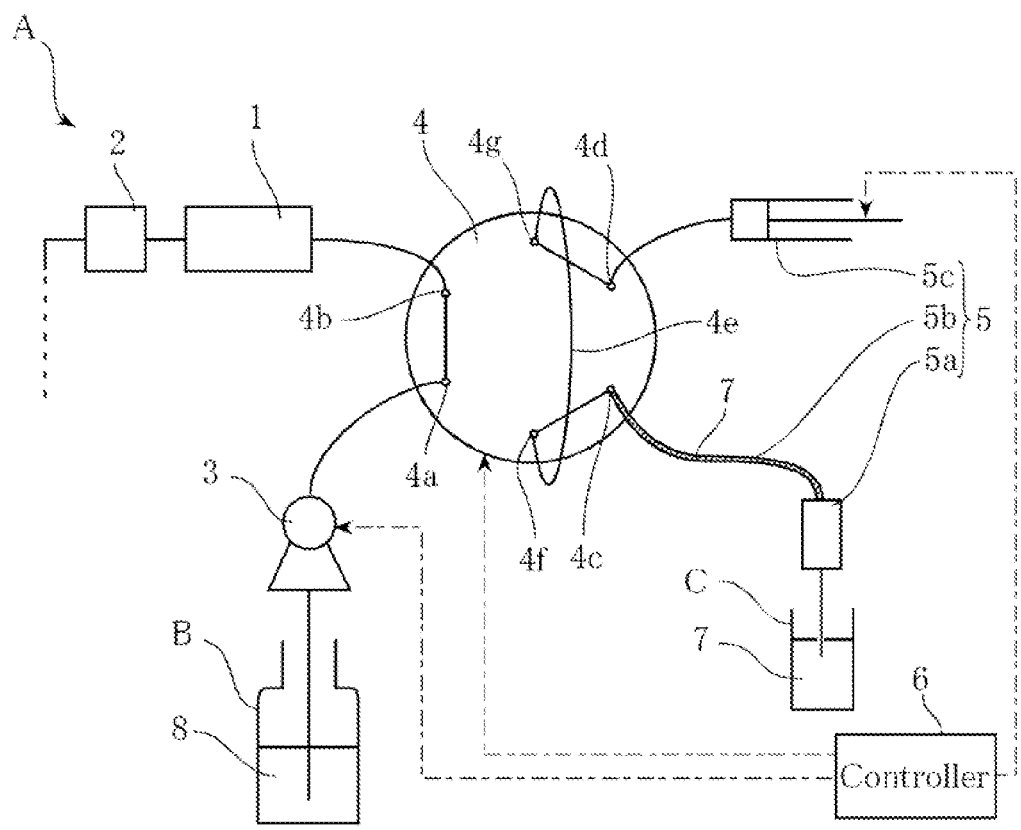
FIG. 2 is a structural view showing the liquid chromatography device of FIG. 1 in a state in which sample is sucked into the device.

First, as shown in FIG. 2, the controller 6 causes the suction unit 5c to draw the sample 7 of an amount necessary for three times of measurement from the sample container C into the tubular portion 5*b* through the sample suction nozzle 5*a*. Then, the controller 6 causes the suction unit 5*c* to draw part of the sample 7 from the tubular portion 5*b* into the injection loop 4*e*. By this, the sample of an amount necessary for two times of measurement is left in the tubular portion 5*b*.

Figure 3:
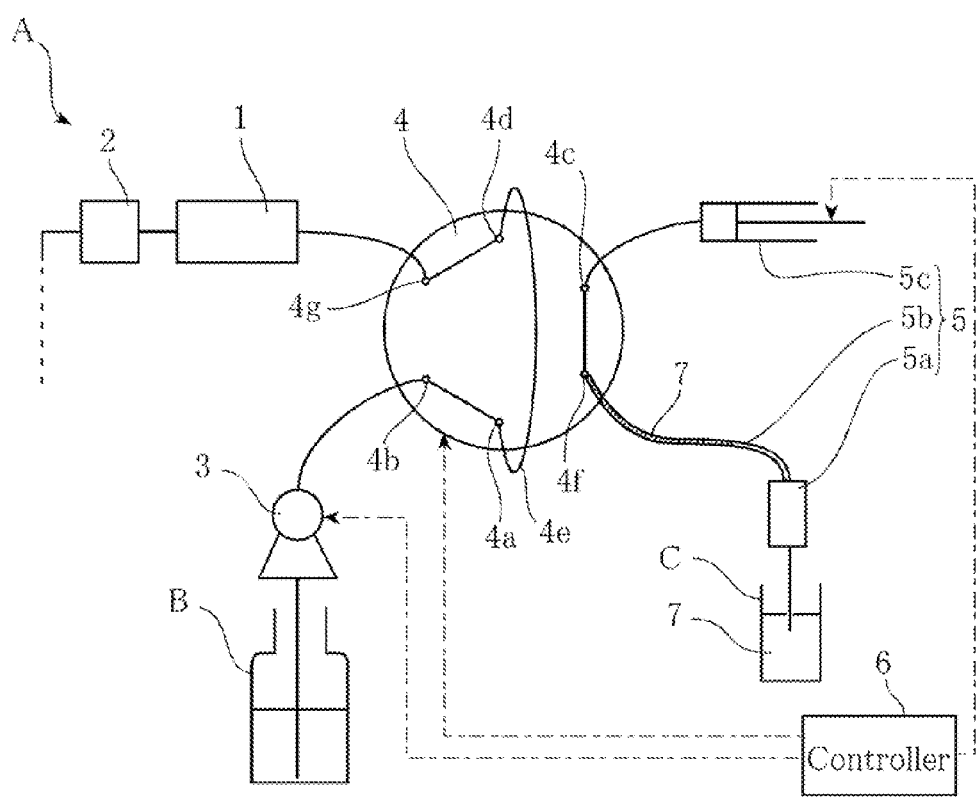
FIG. 3 is a structural view showing the liquid chromatography device of FIG. 1 in a state in which sample is being fed to a column of the device.

Then, as shown in FIG. 3, the controller 6 causes the injection valve 4 to rotate through 60 degrees so that the port 4*g* is connected to the column 1, the port 4*b* is connected to the feed pump 3, the port 4*c* is connected to the suction unit 5*c*, the port 4*f* is connected to the tubular portion 5*b*, and the ports 4*a* and 4*d* are connected to the injection loop 4*e*. This connection establishes a flow path for the eluant 8 to flow into the column 1 through the feed pump 3 and the injection loop 4*e*. Then, the controller 6 causes the feed pump 3 to dispense the eluant 8 drawn from the mobile phase container B, thereby causing the sample 7 in the injection loop 4*e* to be sent into the column 1. Then, after the sample 7 is adsorbed to the filler in the column 1, the controller 6 causes the injection valve 4 to rotate through 60 degrees so that the port 4*b* is connected to the column 1, the port 4*a* is connected to the liquid feed pump 3, the port 4*d* is connected to the suction unit 5*c*, the port 4*c* is connected to the tubular portion 5*b*, the ports 4*f* and 4*g* are connected to the injection loop 4*e*. Then, the controller 6 causes the feed pump 3 to send the eluant 8 from the mobile phase container B into the column 1. The eluant 8 sent into the column 1 desorbs the sample 7 from the filler, whereby effluent is obtained. The effluent is subjected to measurement by the detector 2, whereby the result of the first time of measurement is obtained.

Figure 4:
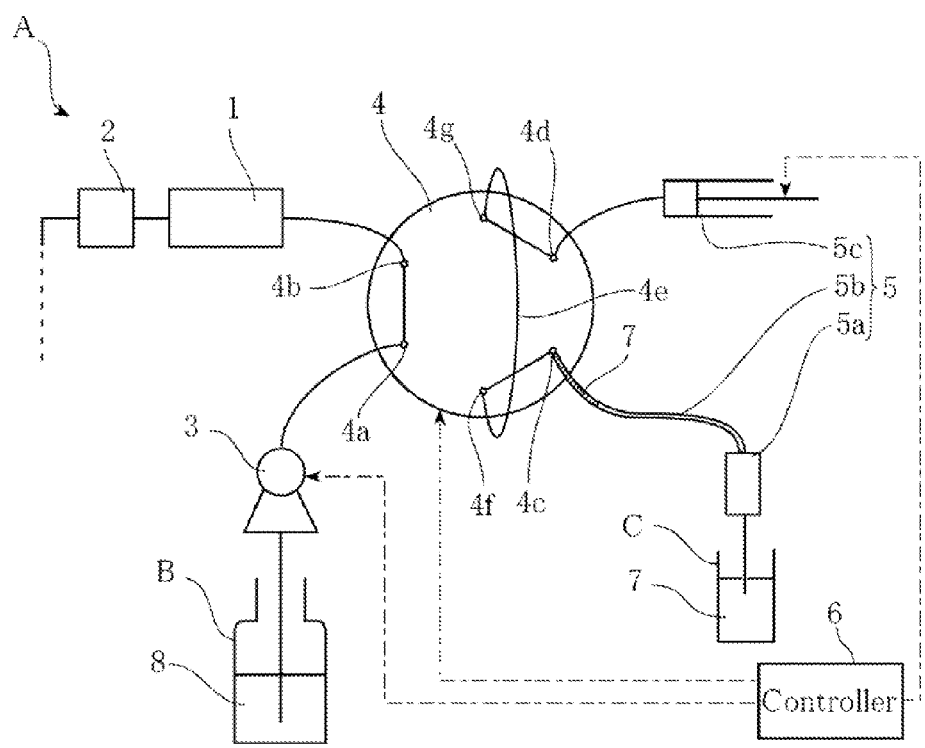
FIG. 4 is a structural view showing the liquid chromatography device of FIG. 1 during the second time of measurement.
Figure 5:
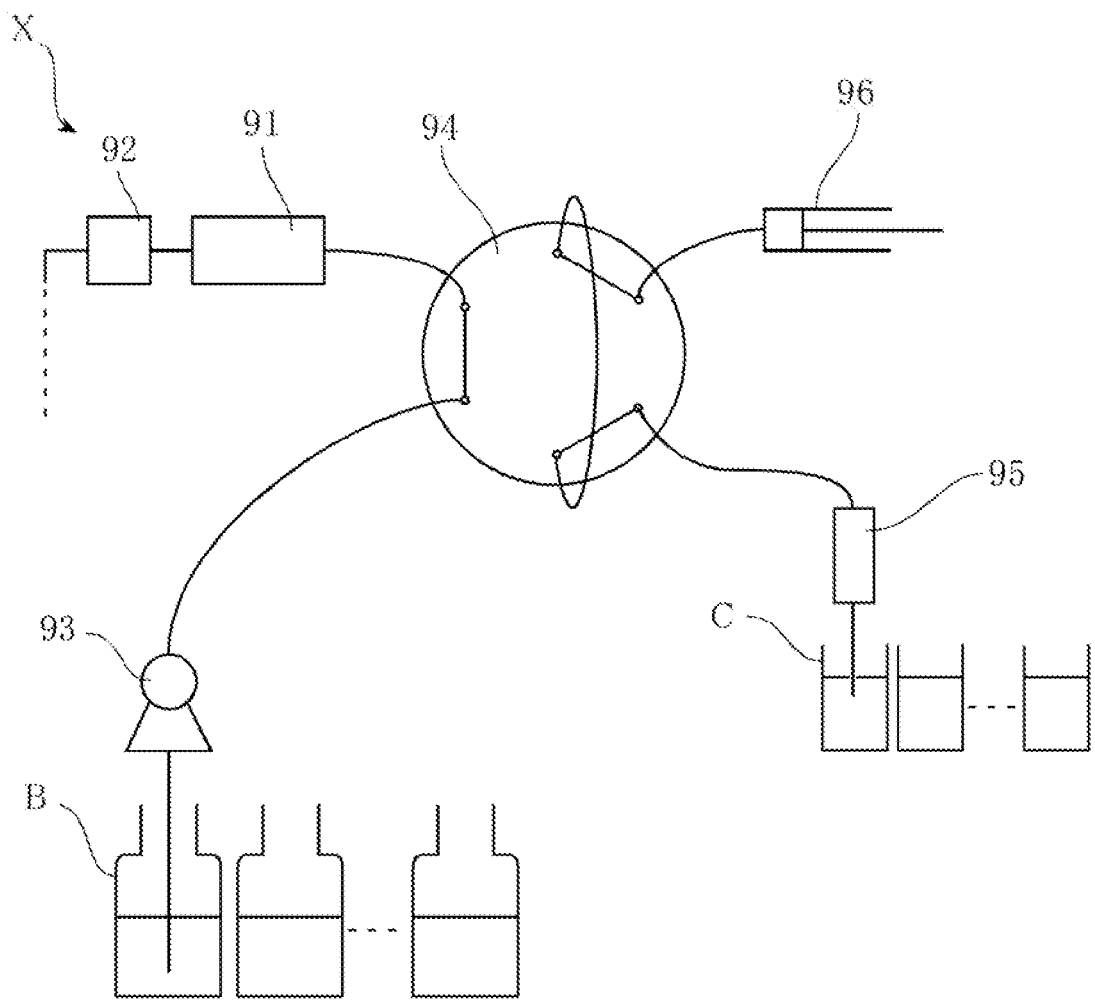
FIG. 5 is a structural view showing an example of conventional liquid chromatography device.

Then, as shown in FIG. 4, the controller 6 causes the suction unit 5*c* to draw part of the sample 7 remaining in the tubular portion 5*b* into the injection loop 4*e*. By this, the sample of an amount necessary for a single time of measurement is left in the tubular portion 5*b*. At this time, since the sample 7 is not a newly drawn sample, cleaning of the injection loop 4*e* is not necessary. Thereafter, measurement is performed under the same control as that for the first time of measurement, whereby the result of the second time of measurement is obtained.

Thereafter, similarly to the above, the third time of measurement is performed using the sample 7 remaining in the tubular portion 5*b*.

The advantages of the liquid chromatography device A are described below.

According to the present embodiment, measurement for accuracy check can be performed three times using a single sample container C. Thus, it is not necessary to prepare a lot of sample containers C for accuracy check. Thus, the liquid chromatography device A considerably saves the effort for the accuracy check and also reduces the cost for the accuracy check.

According to the present embodiment, cleaning work, which usually takes a lot of effort and time, does not need to be performed even a single time before the three times of measurement is completed. Thus, the effort and time taken for the accuracy check is considerably saved. Thus, the liquid chromatography device A allows quick accuracy check.

According to the present embodiment, once the sample 7 is sucked, three times of measurement can be performed, without the need for sucking the sample again. Thus, the accuracy check can be performed efficiently, and the time taken for the accuracy check is considerably reduced. This also contributes to the quick accuracy check of the liquid chromatography device A with reduced cost.

According to the present embodiment, the tubular portion 5*b* is commonly used as the feeding path for the sample 7 and as the sample storage portion during the accuracy check. Thus, the liquid chromatography device A does not require any special structural member used exclusively for the accuracy check.

The analyzing device according to the present invention is not limited to the foregoing embodiment. The specific structure of each part of the analyzing device according to the present invention may be varied in design in many ways. For instance, although the tubular portion 5*b* is configured to store the sample 7 of the amount necessary for three times of measurement in the foregoing embodiment, the tubular portion may be configured to store the sample necessary for the measurement of any number of times greater than two. The portion for storing the sample between the sample suction nozzle 5*a* and the injection valve 4 is not limited to a tubular one, and e.g. a storage tank may be provided instead.

The invention claimed is:

1. An analyzing device comprising:
    a feeder connected to a container in which a sample is contained, the feeder being configured to suck the sample from the container, hold an amount of the sample necessary for two or more measurements, and configured to feeding the sample to an injection valve with multiple ports;
    the feeder further comprise of a tubular portion directly connected to one of the multiple ports of the injection valve;
    a controller for performing control for feeding the sample from the feeder to a measurer;
    wherein, in measuring the sample, the controller performs control so that results of a plurality of measurements are obtained with respect to the single container in which the sample is contained, without changing the container;
    the measurer includes a column containing a filler and an injection valve with multiple ports, capable of introducing a predetermined amount of sample into the column and also capable of feeding a mobile phase into the column, the measurer being configured so that the sample adsorbed to the filler is desorbed by the mobile phase and an effluent thereby produced is subjected to measurement for obtaining measurement results; and
    in checking accuracy by using a sample of a known concentration as the sample, the controller performs control of the feeder and the measurer so that results of a plurality of measurements are obtained with respect to the single container in which the sample of the known concentration is contained, without changing the container.

2. The analyzing device according to claim 1, wherein: the tubular portion is capable of retaining therein the sample of an amount necessary for two or more times of measurement; and
    the controller first performs control of the feeder and the measurer so that part of the sample retained by the feeder is fed to the measurer, and then, after a single measurement, the controller performs control of the feeder and the measurer so that at least part of the remaining sample retained by the feeder is fed to the measurer.

3. A method of controlling an analyzing device comprising a feeder connected to a container in which a sample is contained for sucking the sample from the container and feeding the sample, a tubular portion capable of retaining therein the sample of an amount necessary for two or more times of measurement and a measurer to which the sample is fed from the feeder, the measurer includes a column containing a filler, and an injection valve capable of introducing a predetermined amount of sample into the column and also capable of feeding a mobile phase into the column, the measurer being configured so that the sample adsorbed to the filler is desorbed by the mobile phase and an effluent thereby produced is subjected to measurement for obtaining measurement results; and the feeder is configured to feed the sample to the injection valve with multiple ports, the method comprising a step of first controlling the feeder and the measurer so that part of the sample retained by the feeder is fed to the measurer, and then, after a single measurement, controlling the feeder and the measurer so that at least part of the remaining sample retained by the feeder is fed to the measurer, a step of controlling the measurer when measuring the sample, so that a plurality of measurements are obtained with respect to the single container in which the sample is contained, without changing the container, and a step controlling the feeder and the measurer in checking accuracy by using a sample of a known concentration as the sample, so that results of a plurality measurements are obtained with respect to the single container in which the sample of the known concentration is contained, without changing the container.

4. The method of controlling an analyzing device according to claim 3, the method further comprises controlling the feeder and the measurer so that part of the sample retained by the feeder is fed to the column via the injection valve with multiple ports, and then, after a measurement, controlling the feeder and the measurer so that at least part of the remaining sample retained by the feeder is fed to the column via the injection valve with multiple ports.

* * * * *